US011407785B2

(12) United States Patent
Varni et al.

(10) Patent No.: US 11,407,785 B2
(45) Date of Patent: *Aug. 9, 2022

(54) SYSTEMS AND METHODS FOR EXCHANGE OF BUFFER SOLUTIONS

(71) Applicant: Unchained Labs, Pleasanton, CA (US)

(72) Inventors: John Varni, Los Gatos, CA (US); Stephen Lambert, Castro Valley, CA (US); Robert Busacca, San Francisco, CA (US); Russell Burge, Mountain View, CA (US)

(73) Assignee: Unchained Labs, Pleasanton, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/861,099

(22) Filed: Apr. 28, 2020

(65) Prior Publication Data
US 2020/0255472 A1 Aug. 13, 2020

Related U.S. Application Data

(63) Continuation of application No. 15/311,954, filed as application No. PCT/US2015/031900 on May 21, 2015, now Pat. No. 10,640,531.
(Continued)

(51) Int. Cl.
C07K 1/34 (2006.01)
B01D 61/14 (2006.01)
(Continued)

(52) U.S. Cl.
CPC .............. C07K 1/34 (2013.01); B01D 61/145 (2013.01); B01D 61/18 (2013.01); B01D 65/08 (2013.01);
(Continued)

(58) Field of Classification Search
CPC ........ C07K 1/34; C07K 16/00; C07K 16/065; B01D 61/145; B01D 61/18; B01D 65/08; B01D 2311/14; B01D 2311/10; B01D 2321/18; B01D 2321/2058; B01D 61/20; B01D 61/22; B01D 63/08; B01D 2321/2016; B01D 2321/2041; G01N 1/34;
(Continued)

(56) References Cited

U.S. PATENT DOCUMENTS 4,777,021 A 10/1988 Wertz et al.
4,948,564 A 8/1990 Root et al.
(Continued)

FOREIGN PATENT DOCUMENTS

CN 1279688 A 1/2001
CN 101155915 A 4/2008
(Continued)

OTHER PUBLICATIONS

Final Office Action dated Mar. 29, 2019, for U.S. Appl. No. 15/311,954, filed Feb. 28, 2017, 16 pages.
(Continued)

Primary Examiner — Joseph W Drodge
(74) Attorney, Agent, or Firm — Cooley LLP

(57) ABSTRACT

Systems and methods for exchanging buffer solutions are disclosed. In accordance with some embodiments, the methods and systems for buffer exchange may be automated and/or the methods and systems may include mixing during filtering operations.

11 Claims, 14 Drawing Sheets

Related U.S. Application Data

(60) Provisional application No. 62/001,450, filed on May 21, 2014.

(51) Int. Cl.
| | |
|---|---|
| B01D 61/18 | (2006.01) |
| B01D 65/08 | (2006.01) |
| G01N 1/34 | (2006.01) |
| C07K 16/06 | (2006.01) |
| G01N 1/40 | (2006.01) |
| G01N 35/10 | (2006.01) |
| C07K 16/00 | (2006.01) |
| G01N 35/00 | (2006.01) |

(52) U.S. Cl.
CPC ............ *C07K 16/00* (2013.01); *C07K 16/065* (2013.01); *G01N 1/34* (2013.01); *G01N 1/40* (2013.01); *G01N 35/1009* (2013.01); *G01N 35/1016* (2013.01); *B01D 2311/10* (2013.01); *B01D 2311/14* (2013.01); *B01D 2321/18* (2013.01); *B01D 2321/2058* (2013.01); *G01N 2001/4088* (2013.01); *G01N 2035/00485* (2013.01); *G01N 2035/1025* (2013.01)

(58) Field of Classification Search
CPC ... G01N 2035/1025; G01N 2001/4088; G01N 2035/00485; G01N 1/18; G01N 1/38; G01N 1/40; G01N 1/4005; G01N 2001/368; G01N 2001/381; G01N 2001/4016; G01N 35/1009; G01N 35/1016; G01N 2035/1053; G01N 2035/1058; C12M 1/12; C12M 1/123; C12M 1/36; C12M 1/38; C12M 3/06; C12M 3/062; C12M 23/12; C12M 25/02; C12M 25/04; C12M 27/14; C12M 27/16; C12M 41/12; C12M 41/44; C12M 41/48; B01L 3/50255
USPC ...... 210/85, 96.1, 321.75, 321.84, 650, 651, 210/739, 741, 744, 745, 746; 422/81, 422/82.01, 82.05, 82.13, 105, 106, 509, 422/513, 534, 535; 435/288.2, 288.4, 435/288.5, 297.1, 297.5
See application file for complete search history.

(56) References Cited

U.S. PATENT DOCUMENTS

| | | | |
|---|---|---|---|
| 5,342,581 A | 8/1994 | Sanadi | |
| 6,159,368 A | 12/2000 | Moring et al. | |
| 6,251,295 B1 | 6/2001 | Johnson | |
| 6,780,584 B1* | 8/2004 | Edman | B01J 19/0046 |
| | | | 422/50 |
| 8,404,198 B2 | 3/2013 | Amshey et al. | |
| 10,640,531 B2 | 5/2020 | Varni et al. | |
| 2001/0001644 A1 | 5/2001 | Coffman et al. | |
| 2002/0043487 A1* | 4/2002 | Schick | B01D 61/16 |
| | | | 210/85 |
| 2002/0113004 A1 | 8/2002 | Bowers et al. | |
| 2002/0132242 A1 | 9/2002 | Gerdes et al. | |
| 2002/0175124 A1* | 11/2002 | Tkacik | B01D 63/14 |
| | | | 210/651 |
| 2004/0072278 A1* | 4/2004 | Chou | G01N 15/1456 |
| | | | 435/29 |
| 2005/0023194 A1* | 2/2005 | Petersen | B01D 63/081 |
| | | | 210/85 |
| 2005/0051799 A1* | 3/2005 | Huang | H01L 29/1004 |
| | | | 257/198 |
| 2005/0161377 A1 | 7/2005 | Fujimoto et al. | |
| 2006/0171850 A1 | 8/2006 | Waterbury et al. | |
| 2007/0248958 A1* | 10/2007 | Jovanovich | B01L 3/50273 |
| | | | 435/6.19 |
| 2008/0087554 A1* | 4/2008 | Norris | G01N 1/40 |
| | | | 205/792 |
| 2008/0264792 A1* | 10/2008 | Moon | B01D 63/02 |
| | | | 204/452 |
| 2009/0253181 A1 | 10/2009 | Vangbo et al. | |
| 2010/0170852 A1 | 7/2010 | Suh et al. | |
| 2010/0193413 A1* | 8/2010 | Lendenfeld | C12M 41/38 |
| | | | 210/85 |
| 2011/0220501 A1* | 9/2011 | Witkowski | G01N 27/44713 |
| | | | 204/457 |
| 2011/0315632 A1 | 12/2011 | Freije et al. | |
| 2012/0244529 A1 | 9/2012 | Fuchs et al. | |
| 2013/0040376 A1 | 2/2013 | Amshey et al. | |
| 2013/0045532 A1* | 2/2013 | Hyman | C12Q 1/6888 |
| | | | 435/297.1 |
| 2013/0075310 A1* | 3/2013 | Volker | B01D 61/025 |
| | | | 210/86 |
| 2013/0264286 A1* | 10/2013 | Tai | B01L 3/50255 |
| | | | 210/636 |
| 2014/0286124 A1 | 9/2014 | Donohue et al. | |
| 2014/0335527 A1* | 11/2014 | Goel | B01L 3/502738 |
| | | | 435/6.12 |
| 2018/0111121 A1* | 4/2018 | Amshey | B01L 3/502715 |

FOREIGN PATENT DOCUMENTS

| | | |
|---|---|---|
| CN | 102203605 A | 9/2011 |
| CN | 102216450 A | 10/2011 |
| JP | 2005-204578 A | 8/2005 |
| JP | 2005-204579 A | 8/2005 |
| JP | 2012-506995 A | 3/2012 |
| JP | 2014-501517 A | 1/2014 |
| WO | WO-99/19343 A1 | 4/1999 |
| WO | WO-02/071072 A2 | 9/2002 |
| WO | WO-02/071072 A3 | 9/2002 |
| WO | WO-2006/108707 A1 | 10/2006 |
| WO | WO-2010/025302 A2 | 3/2010 |
| WO | WO-2010/025302 A3 | 3/2010 |
| WO | WO-2010/036760 A1 | 4/2010 |
| WO | WO-2012/073115 A1 | 6/2012 |
| WO | WO-2012/151199 A1 | 11/2012 |
| WO | WO-2012/171030 A2 | 12/2012 |
| WO | WO-2012/171030 A3 | 12/2012 |

OTHER PUBLICATIONS

International Search Report dated Nov. 24, 2015, for PCT Patent Application No. PCT/US2015/031900, filed on May 21, 2015, 6 pages.
Non-Final Office Action dated Nov. 6, 2018, for U.S. Appl. No. 15/311,954, filed Feb. 28, 2017, 14 pages.
Non-Final Office Action dated Jul. 22, 2019, for U.S. Appl. No. 15/311,954, filed Feb. 28, 2017, 20 pages.
Notice of Allowance dated Dec. 18, 2019, for U.S. Appl. No. 15/311,954, filed Feb. 28, 2017, 9 pages.
Written Opinion of the International Searching Authority dated Nov. 24, 2015, for PCT Patent Application No. PCT/US2015/031900, filed on May 21, 2015, 8 pages.

* cited by examiner

SYSTEMS AND METHODS FOR EXCHANGE OF BUFFER SOLUTIONS

CROSS-REFERENCE TO RELATED APPLICATIONS

This application is a continuation of U.S. application Ser. No. 15/311,954, filed Feb. 28, 2017, which is a National Stage Application under 35 U.S.C. § 371 of International Application No. PCT/US2015/031900, filed May 21, 2015, which claims the benefit of U.S. Provisional Application No. 62/001,450, filed May 21, 2014, each of which is incorporated herein by reference in its entirety.

FIELD OF THE DISCLOSURE

The field of the disclosure relates to systems and methods for exchanging buffer solutions and, according to particular embodiments, automated methods and systems for buffer exchange and/or methods and systems that include mixing (e.g., vortexing) during filtering operations.

BACKGROUND

Various biological components such as proteins may be formulated for analysis and/or further processing. Such biological components may be prepared in buffer solutions to maintain a relatively narrow pH range at which the component is biologically active and remains viable. It may be desirable to exchange buffer solutions for further downstream processing of the biological component. Such buffer exchange may be relatively difficult as the biological component must be filtered from the native buffer solution and exchanged with a second buffer solution without altering the activity and viability of the biological component.

A need exists for methods and systems for automated exchange of buffer solutions with parallel processing of biological components.

SUMMARY

One aspect of the present disclosure is directed to an automated method for exchange of buffer solutions from admixtures comprising a buffer solution and a biological component. A plurality of individual reservoirs containing an admixture comprising a biological component and a first buffer solution are provided. The reservoirs contain a semi-permeable membrane. The reservoirs are pressurized to force the first buffer solution through the semi-permeable membrane to produce a buffer-depleted residue. Amounts of first buffer that were removed from the individual reservoirs are detected. A second buffer is added to the reservoirs. An amount of second buffer added to the individual reservoirs is determined by the detected amount of first buffer that was removed from the reservoir.

Another aspect of the present disclosure is directed to a system for automated exchange of buffer solutions from admixtures comprising a buffer solution and a biological component. The system includes a pressure chamber for receiving a plurality of reservoirs having a semi-permeable membrane and for creating a pressure difference across the membrane to force a first buffer solution through the membrane and produce a first buffer-depleted residue in the reservoir. The system includes a sensor for detecting the level of fluid in the reservoirs and a dispensing system for adding a second buffer solution to the reservoirs. The dispensing system is configured to add an amount of second buffer to the reservoirs based on the sensed level of the buffer-depleted residue in the reservoirs.

Yet another aspect of the present disclosure is directed to a method for removal of a low molecular weight carrier from an admixture comprising a high molecular weight component or microorganism and the low molecular weight carrier. A plurality of reservoirs containing an admixture comprising a high molecular weight component and low molecular weight carrier are provided. The reservoirs contain a semi-permeable membrane. The reservoirs are pressurized to force the low molecular weight carrier through the semi-permeable membrane to produce a carrier-depleted residue. The admixture is mixed while pressurizing the reservoirs to remove build-up of residue at a surface of the semi-permeable membrane.

Yet a further aspect of the present disclosure is directed to a system for removing a low molecular weight carrier from an admixture comprising a high molecular weight component or microorganism and the low molecular weight carrier. The system includes a pressure chamber for receiving a plurality of reservoirs having a semi-permeable membrane and for creating a pressure difference across the membrane to force the low molecular weight carrier through the membrane and to produce a carrier-depleted residue in the reservoir. The system also includes a mixer for mixing the admixtures while removing the carrier from the admixture.

BRIEF DESCRIPTION OF THE DRAWINGS

Corresponding reference characters indicate corresponding parts throughout the drawings.

DETAILED DESCRIPTION

Figure 9:
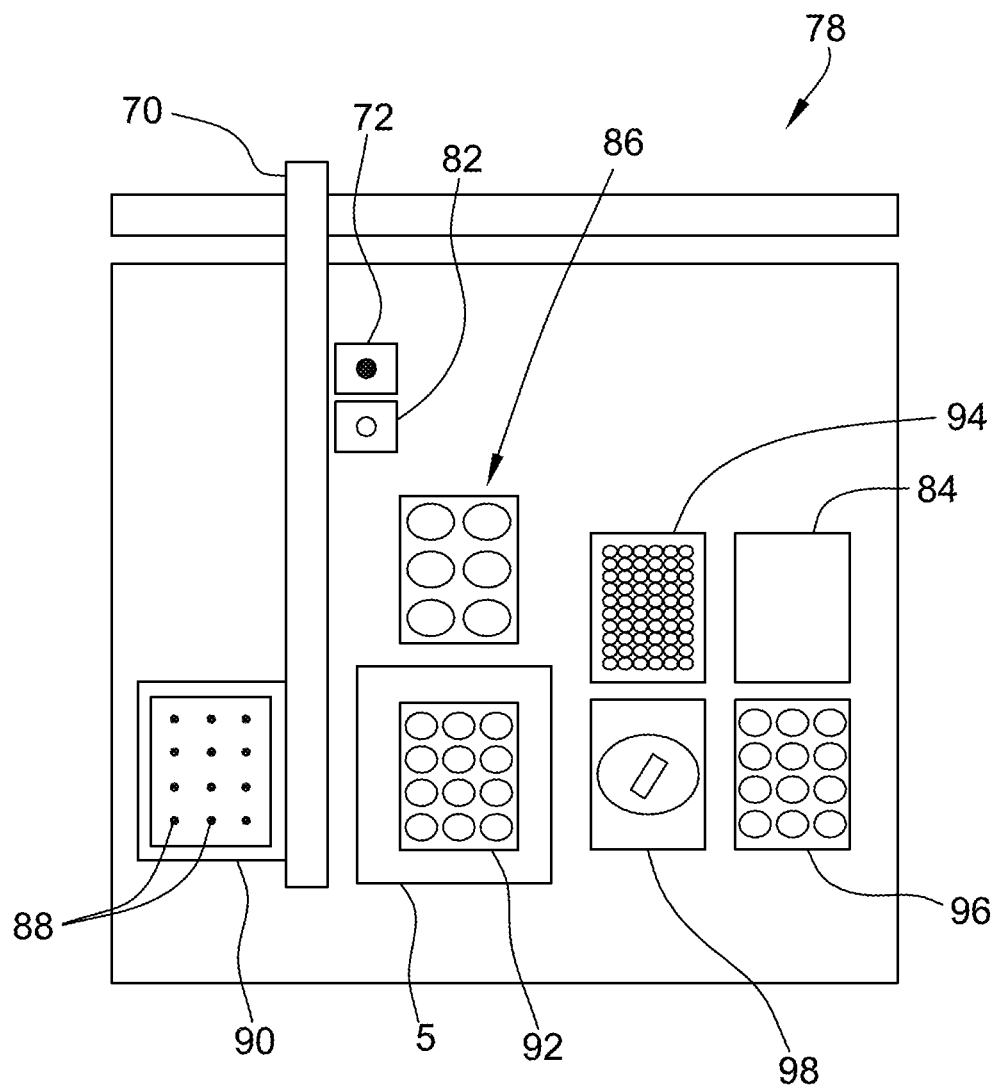
FIG. 9 is a schematic view of a buffer exchange system.

An embodiment of a system 78 for exchanging buffer solutions is shown in FIG. 9. The system is suitable, e.g., for automated exchange of buffer solutions from admixtures that contain a buffer and a biological component. The system includes a pressure assembly 5 for housing a plate 92 of buffer exchange reservoirs. The biological component of the admixture may be selected from proteins, peptides, antigens, antibodies, enzymes, microorganisms, DNA, RNA and the like. As used herein, the initial admixture includes a first buffer solution that is filtered from the admixture as a filtrate leaving a retentate or "first buffer-depleted residue" in the admixture reservoir. A second buffer solution is added to the reservoir based on a detected amount of filtrate and/or retentate. The second buffer may include a different composition, pH, concentration and/or purity relative to the first buffer. The initial admixture may also include other components (e.g., excipients and the like) that are also retained during filtration.

The second buffer may be added in the same volumetric amount as the first buffer to maintain the concentration of the biological components or may be added in a different ratio to concentrate or dilute the component. In some embodiments of the present disclosure, the volumetric ratio of the first buffer removed from each reservoir and the second buffer added to the reservoir is about 1:1. In other embodiments, the volumetric ratio of the first buffer removed from each reservoir and the second buffer added to the reservoirs is less than 1:1 to dilute the biological component. In yet other embodiments, the volumetric ratio is greater than 1:1 to concentrate the biological component.

Figure 1:
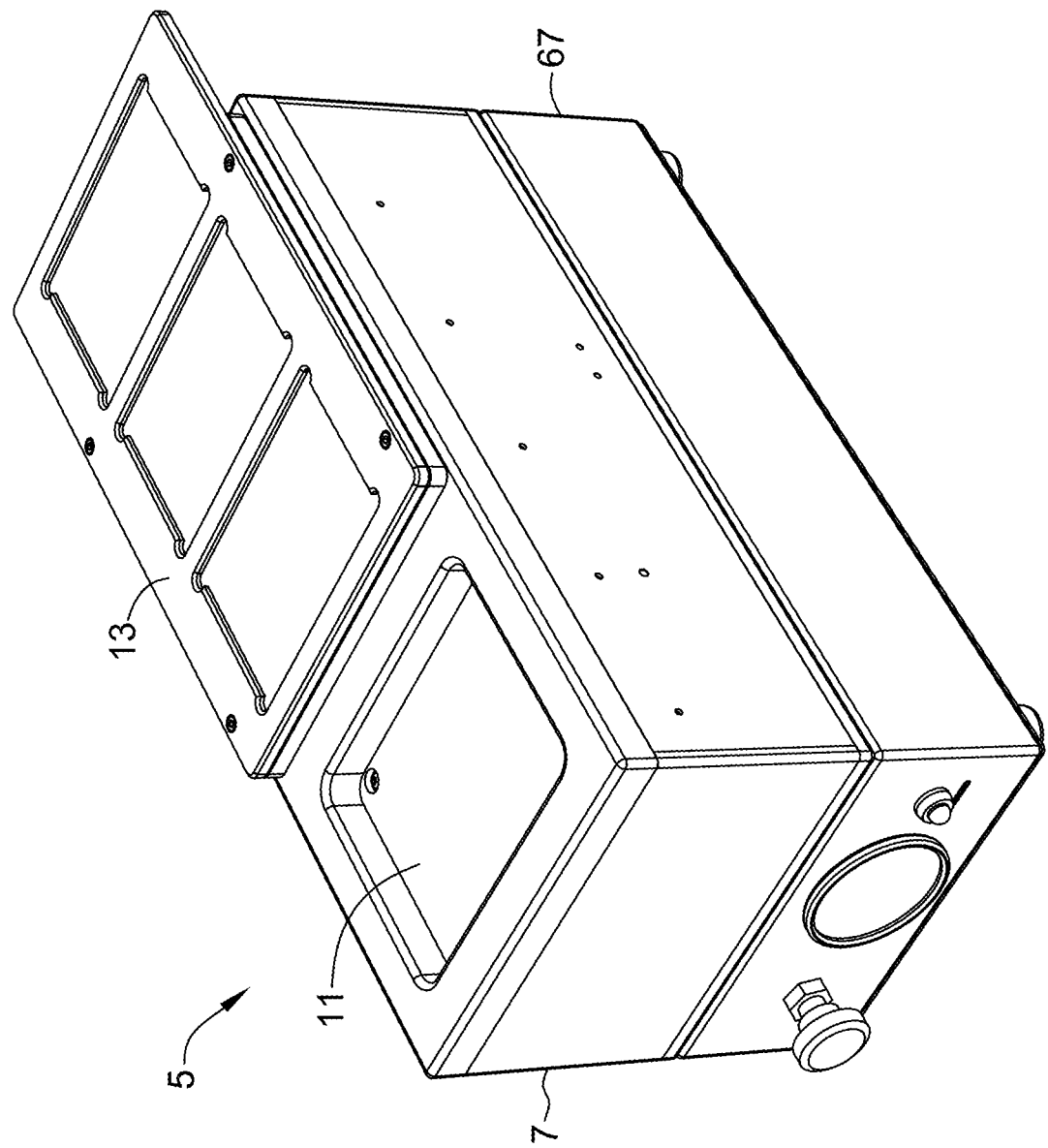
FIG. 1 is a perspective view of a pressure assembly.

The system for buffer exchange includes a pressure assembly generally referred to as "5" in FIG. 1. It should be noted that while the pressure assembly may be described with reference to exchange of buffer solutions, the pressure assembly 5 may also be used to separate a high molecular weight component from a low molecular weight component (the terms "high" and "low" being used with reference to each other). Exemplary processes include filtration of effluent from paper pulp mills, cheese manufacturing (e.g., filtering milk), pathogen (e.g., bacteria, yeast, fungus) removal from milk, process and waste water treatment, enzyme recovery, fruit juice concentration and clarification, dialysis and other blood treatments, clarification of biological solutions such as lysates and precipitates and collection of yeast and bacterial cells from cultures at a microscale for pelleting or further processing. Such purification methods may involve mixing (e.g., vortexing) during the filtering operation to prevent fouling at the surface of the semi-permeable membrane as described below.

The pressure assembly 5 includes an upper housing 7 that defines a chamber 19 (FIG. 2) and includes a chamber door 11 (FIG. 1) for sealing the chamber. The assembly 5 includes a functional cover 13 that may be used to secure additional reservoirs (e.g., microtiter plates) used during the buffer exchange and/or includes blotting mats to clean out the reservoirs. The functional cover 13 may be removable to allow access to system components within the chamber 19.

Figure 8:
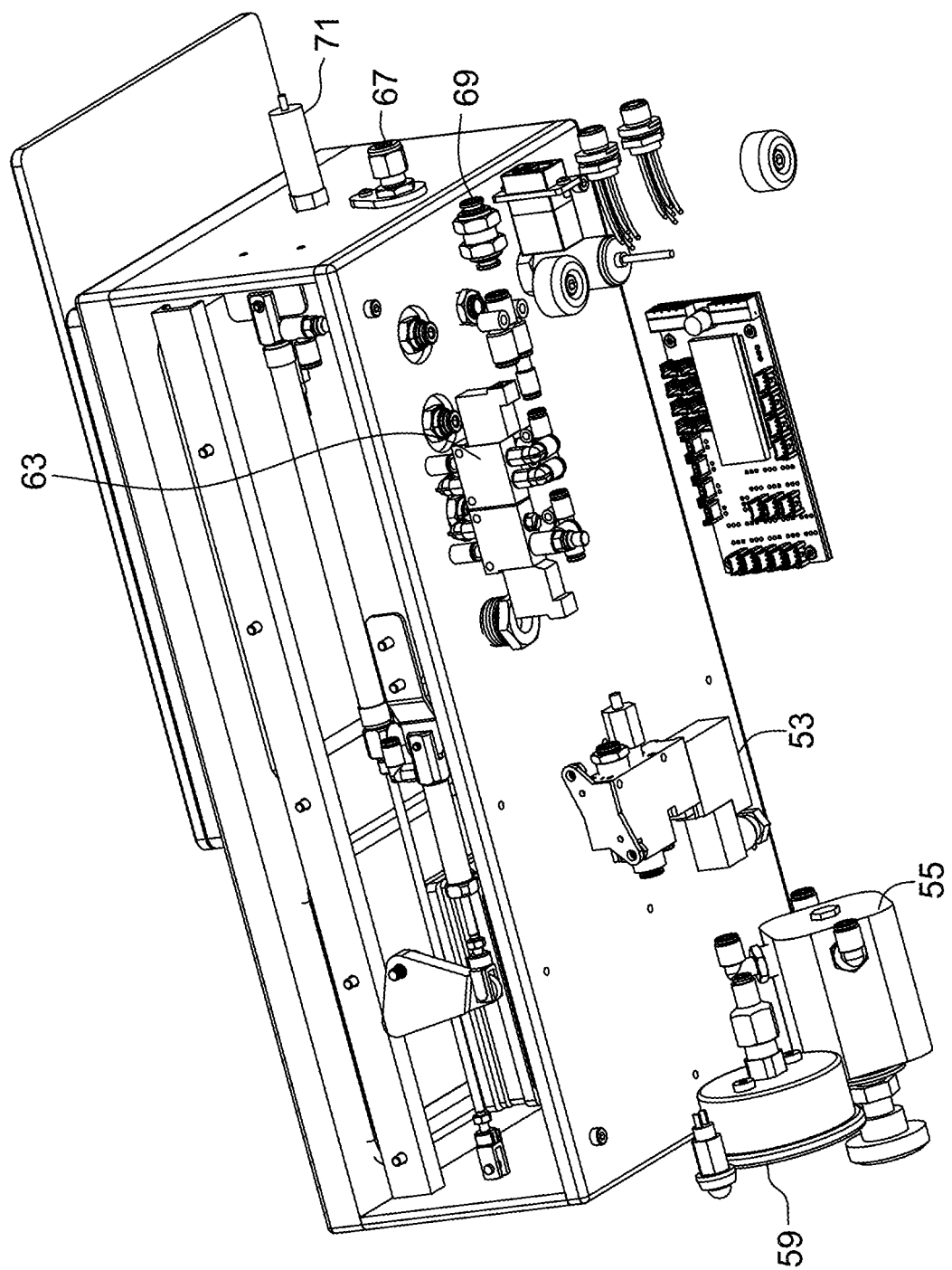
FIG. 8 is a perspective view of the filtration unit with the lower housing not shown.

The chamber door 11 may be raised for sealing the chamber or may be lowered by use of actuator 45 (FIG. 3, side panel not shown) and pivot bracket 45 that is connected to the door 11. Upon lowering the chamber door 11, the actuator 49 may be operated to retract the chamber door 11 upon a rail 41. Upon retraction of the chamber door 11, the filtration unit 21 is accessible for loading filtration wells (e.g., a microtiter plate) and adding buffer to the admixtures. As shown, the actuators 45, 49 are cylinders. In other embodiments, other suitable actuator systems are used. The cylinders may be pneumatic with air supplied through air port 69 (FIG. 8).

Figure 4:
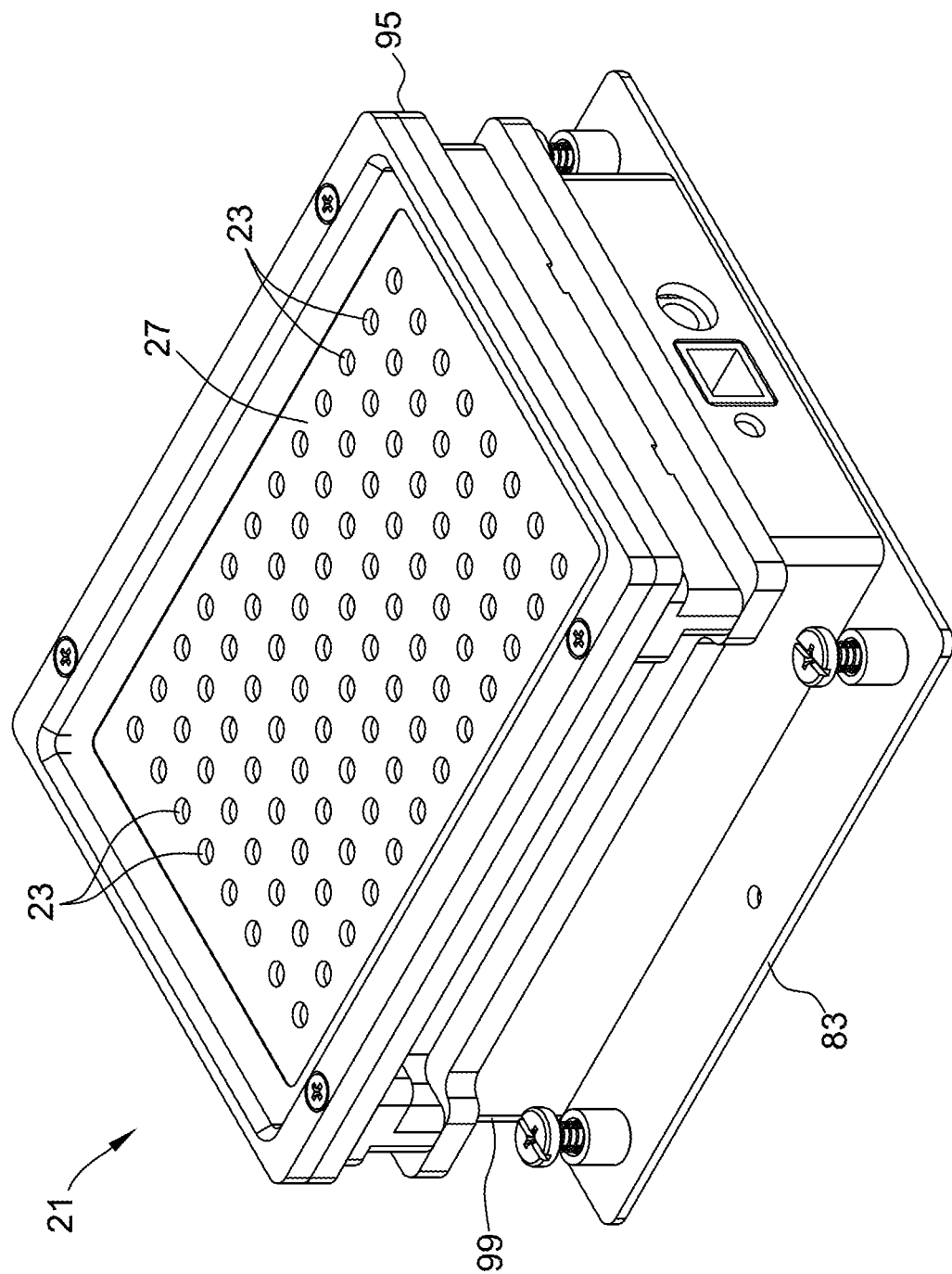
FIG. 4 is a perspective view of a filtration unit of the pressure assembly.

The pressure assembly 5 includes a filtration unit 21 for securing and filtering admixtures within filtration reservoirs or "wells" (not shown). Referring to FIG. 4, the filtration wells (also referred to herein as "substrate") (not shown) are lowered manually into the openings 23 of a receiver plate 27 of the filtration unit 21. As shown in FIG. 4, the receiver plate 27 includes 96 openings 23 for receiving 96 filtration wells such as in a microtiter plate. In various embodiments, the receiver plate 27 includes at least 2 openings or at least about 3, 5, 10, 12, 16, 48 or at least about 96 openings or more. In this regard, use of the term "microtiter plate" herein should not be considered limiting and any suitable substrate for delivering individual reservoirs to the system may be used. In other embodiments, the reservoirs are integral with the system (i.e., form part of the system itself).

The filtration wells may be placed within the openings 23 of the receiver plate 27 manually by lowering the wells through the chamber door opening or by use of an automated loading assembly (not shown).

Generally, each filtration well includes a semi-permeable membrane that forms the bottom of the well to allow for filtration of the biological admixture. Upon pressurizing the chamber 19, a pressure difference forms across the membrane to force buffer solution through the membrane and produce a buffer-depleted residue in the reservoir. The filtration substrate may have 2 wells or at least about 3, 5, 10, 12, 16, 48 or at least about 96 wells or more. The volume of the wells may be about 75 ml or less or, as in other embodiments, about 25 ml or less, about 16 ml or less, about 8 ml or less, about 4 ml or less, about 1 ml or less, about 750 µl or less, about 500 µl or less or about 250 µl or less.

The semi-permeable membrane generally will have a pore size less than the size of the biological component desired to be retained in the reservoirs. For example, proteins may have a size of 20 kDa or more and pore sizes of less than 20 kDa would be used to retain the protein. Depending on the biological component, the semi-permeable membrane may be an ultrafiltration or a nanofiltration-sized membrane. In various embodiments of the present disclosure, the membrane may have pore sizes of about 1000 kDa or less, about 100 kDa or less or about 10 kDa or less. Commercially available ultrafiltration membranes include the ULTRA-CEL-10 Membrane from EMD Millipore (Billerica, Mass.) that is compatible with standard receiver plates.

Figure 2:
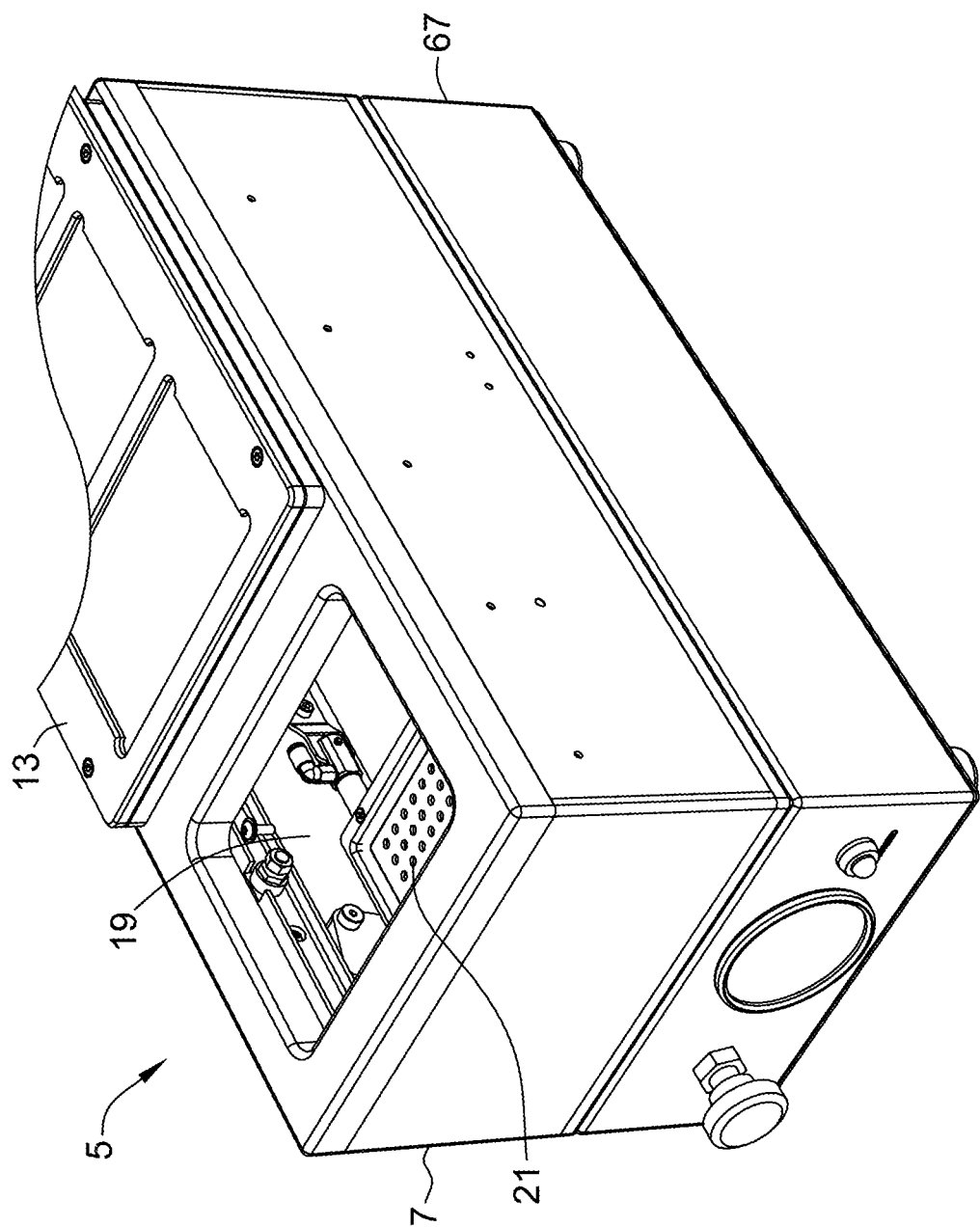
FIG. 2 is a perspective view of the pressure assembly with the chamber door open.
Figure 3:
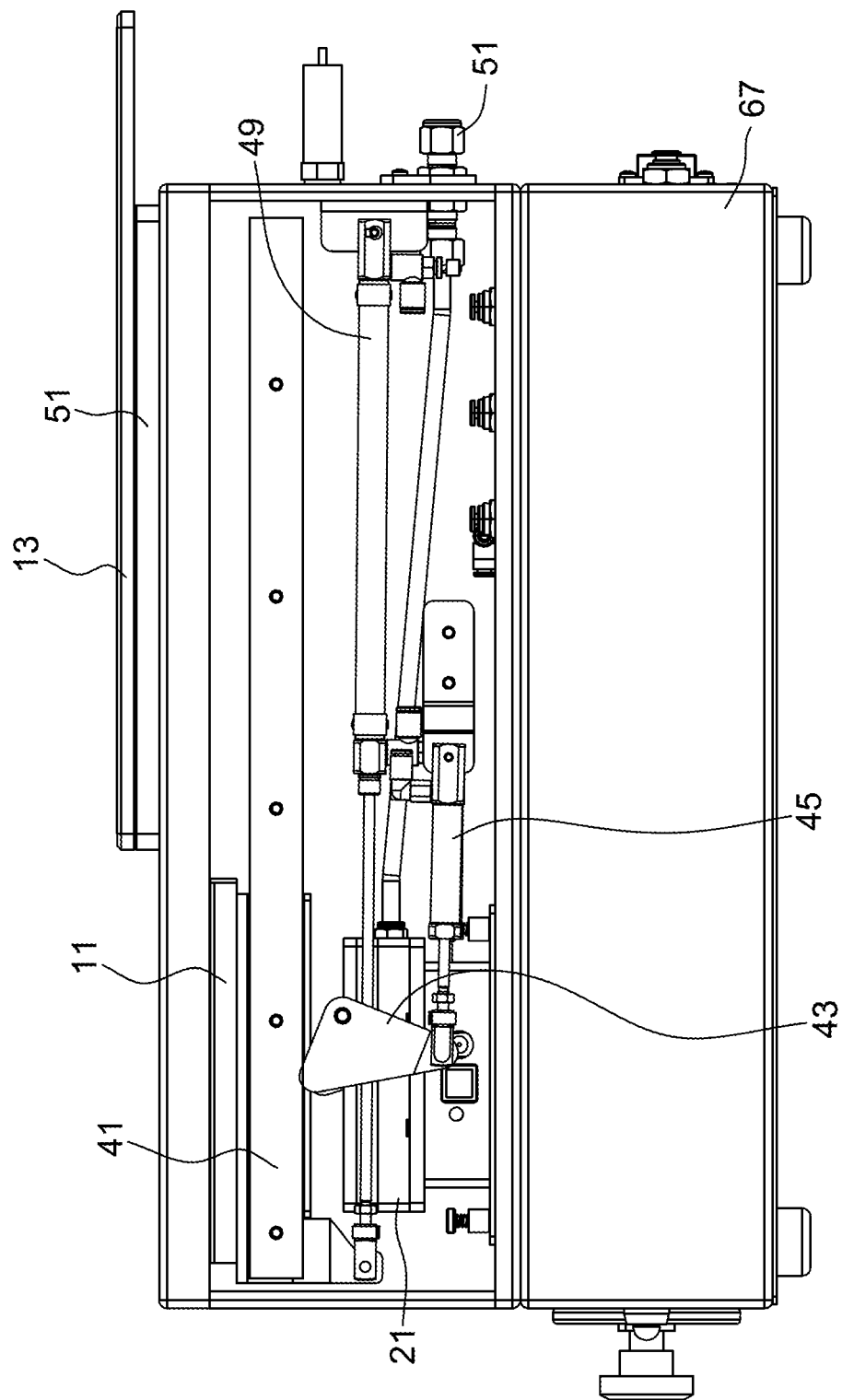
FIG. 3 is a side view of the pressure assembly.

Upon loading the reservoirs containing the semi-permeable membrane into the filtration unit 21, the chamber 19 is pressurized. Air or inert gas is supplied to port 69 (FIG. 8) which is in fluid communication with a pressure regulator 55 (supply and return lines not being shown). The regulated pressure is indicated by a pressure display 59. The pressure regulator 55 is in fluid communication with a solenoid valve 53 for pressurizing the pressure chamber 19 (FIG. 2). The system also includes actuator solenoids 63 for controlling the actuators 45, 49 (FIG. 3). The system includes a pressure relief valve 71 to prevent over-pressurization of the system. The regulator 55, display 59, and solenoids 53, 63 are housed below the pressure chamber in a lower housing 67 (FIG. 1).

Figure 7:
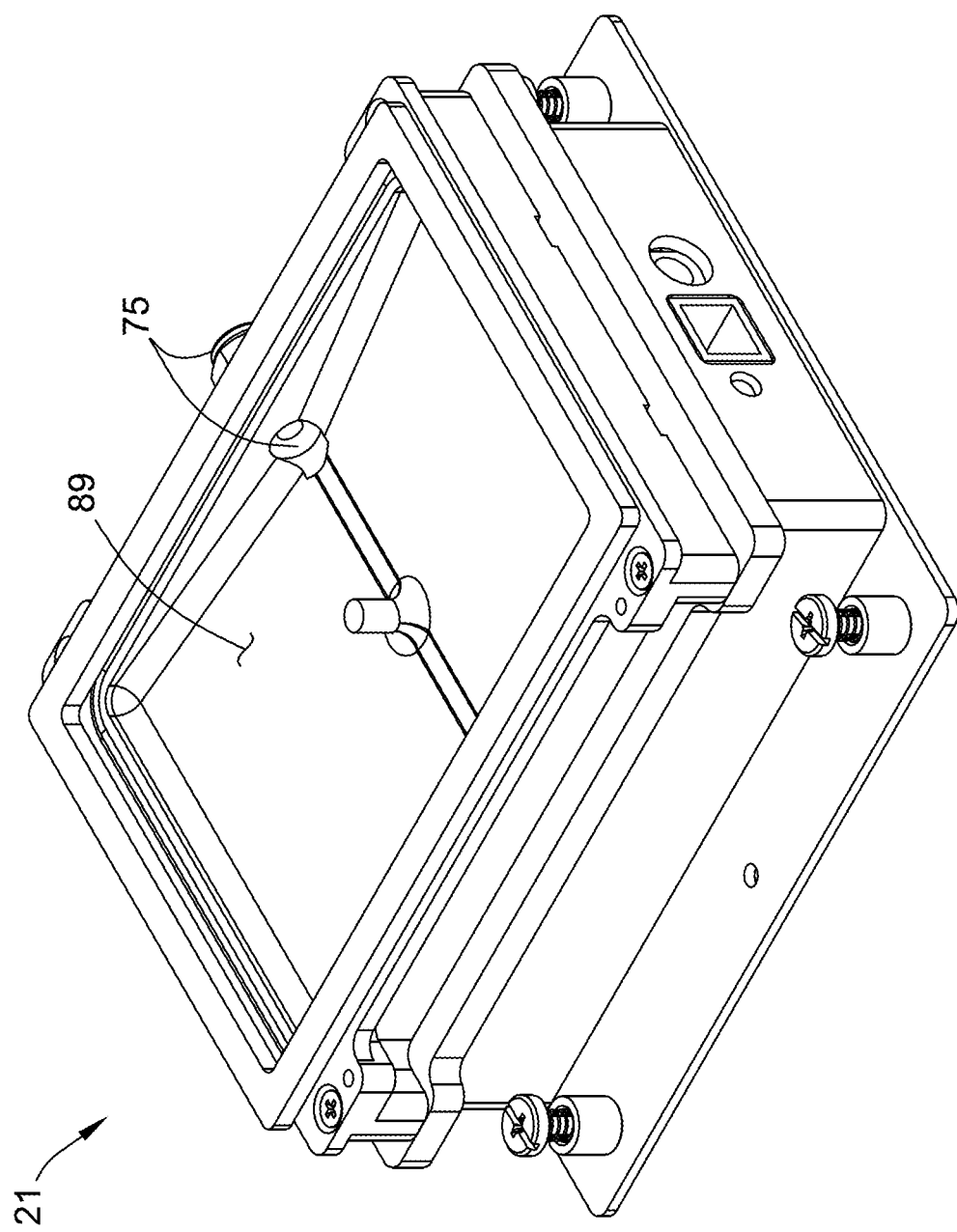
FIG. 7 is a perspective view of the filtration unit with the receiver plate not shown.

The chamber 19 may be pressurized to a pressure of at least about 5 psig or, as in other embodiments, at least about 10 psig, at least about 30 psig, at least about 50 psig or at least about 75 psig to remove filtrate (e.g., from about 5 psig to about 100 psig, from about 10 psig to about 100 psig, or from about 5 psig to about 75 psig). Filtrate may be collected in a filtrate chamber 89 (FIG. 7) and removed from the filtration unit 21 through port 75. Collected filtrate may exit the pressure system through port 67 (FIG. 8) and be introduced into a waste container (not shown).

In some embodiments, the pressure chamber 19 is pressurized to force the buffer solution through the semi-permeable membrane while simultaneously mixing the biological admixture to prevent fouling (i.e., build-up of residue (e.g., protein)) at a surface of the semi-permeable membrane.

Mixing is suitably accomplished by vortexing. The filtration unit 21 includes a vortexing unit 99 (FIG. 4) that rapidly oscillates in a circular or orbital motion to create a vortex within the admixture. Generally, vortexing occurs in a direction normal to the flow direction of filtrate to reduce build-up of retentate on the membrane. The vortexing unit 99 includes a vortex drive (not shown) to oscillate the receiver plate 27 and reservoirs (not shown) received in the openings 23 of the plate.

Figure 5:
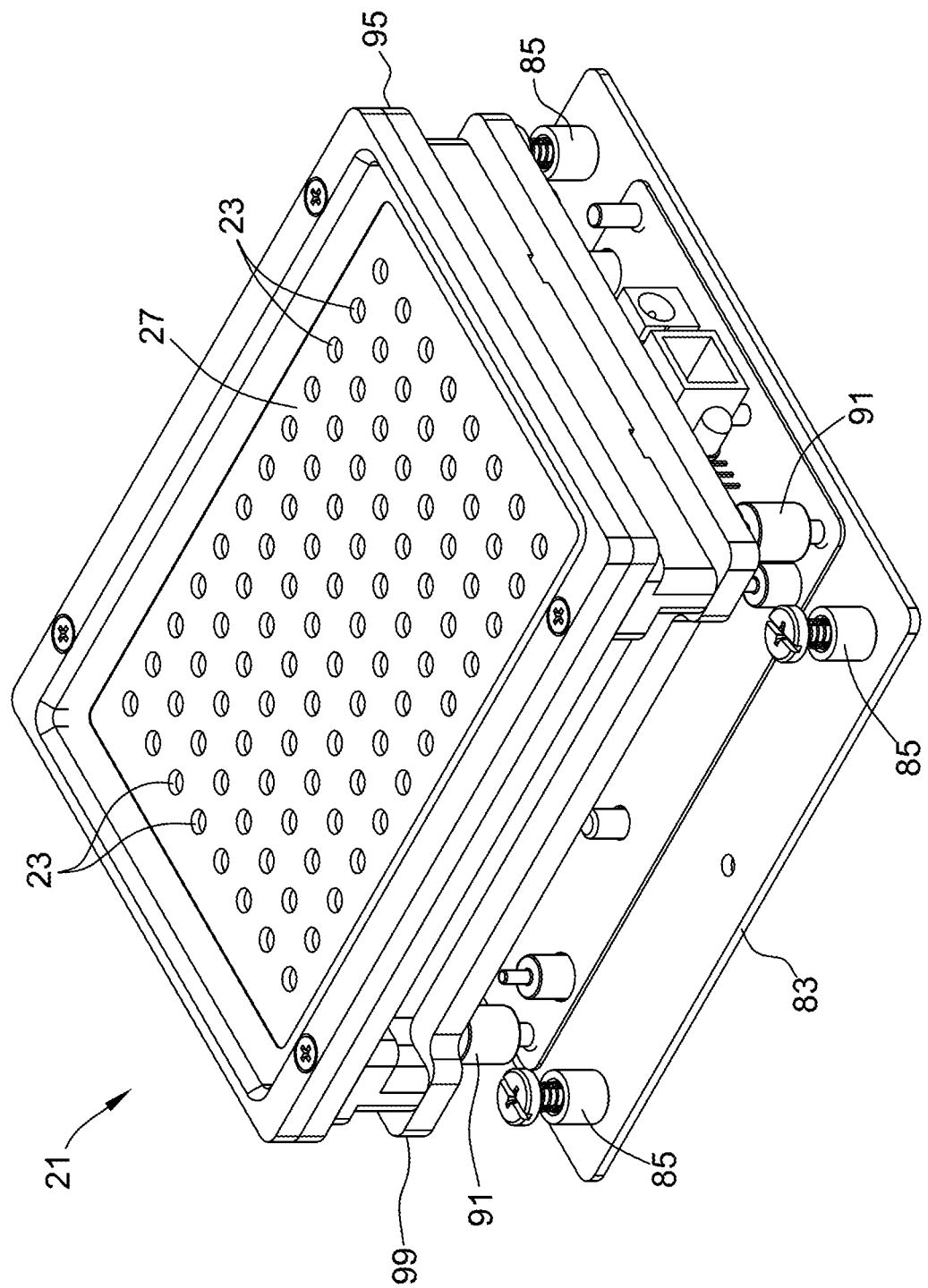
FIG. 5 is a perspective view of the filtration unit with a panel not shown.
Figure 6:
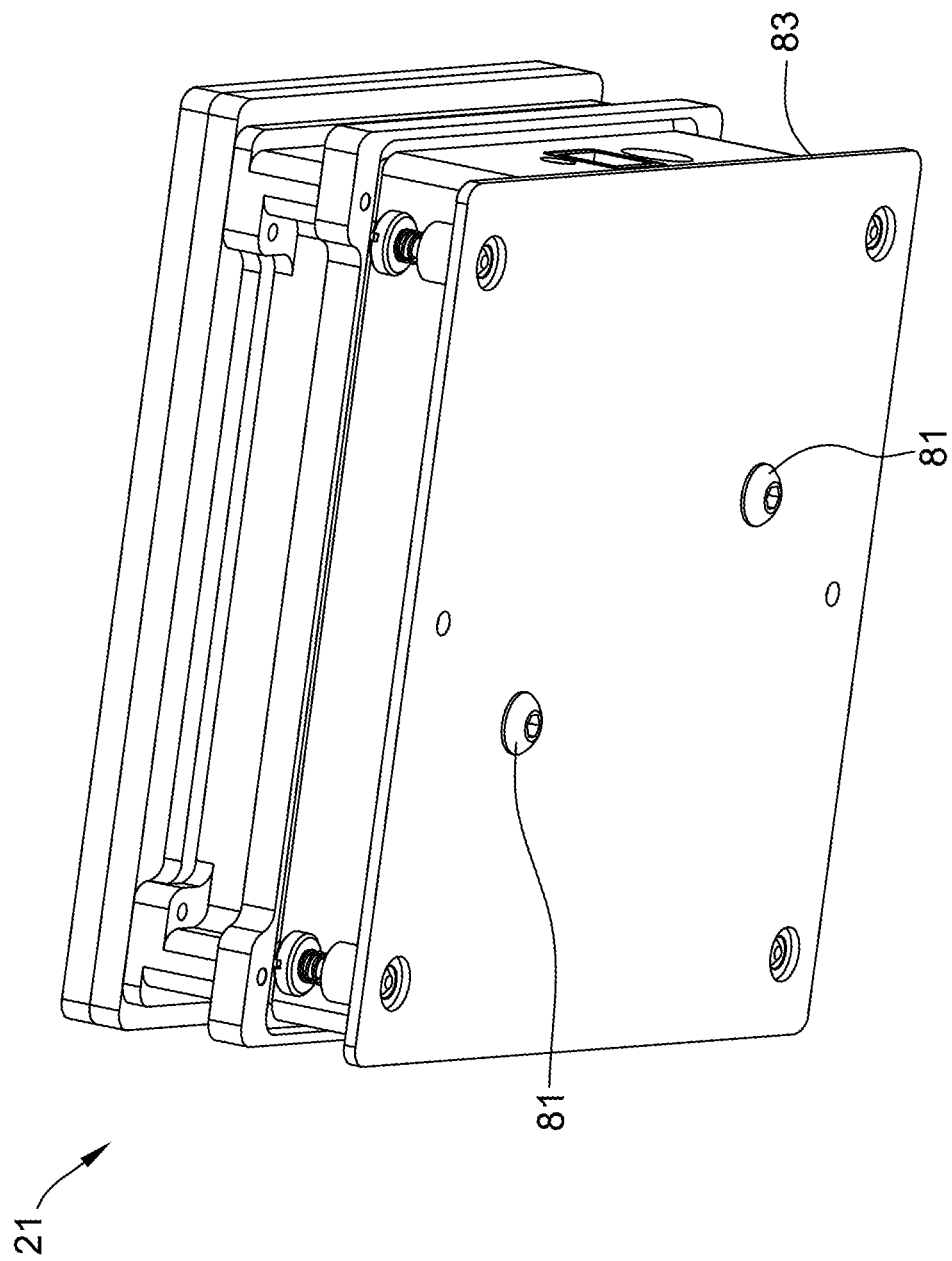
FIG. 6 is another perspective view of the filtration unit.

The vortexing unit 99 may oscillate at about 500 rpm or more, about 1000 rpm or more, about 1500 rpm or more or about 2000 rpm or more (e.g., from about 500 rpm to about 2500 rpm or from about 1000 rpm to about 2000 rpm). The oscillations of the vortexing unit 99 are isolated from the remainder of the system by isolators 91 (FIG. 5). Screw bolts 81 (FIG. 6) are used to secure a base plate 83 to the stationary portion of the vortexing unit 21. Captive screws (FIG. 4) attach the base plate 83 to the housing of the pressure chamber.

The system for automated buffer exchange includes a sensor for detecting the amount (e.g., volume or mass) of filtrate (i.e., first buffer solution) removed from each reservoir and/or the amount of retentate (i.e., first buffer-depleted residue) retained in the reservoir. The sensor may operate by any suitable method including acoustic sensing, capacitance, light, reflectance, displaced air volume or weight (i.e., mass). In this regard, the "amount" of filtrate and/or retentate detected may refer to the volume, mass or level of the material. In some embodiments of the present disclosure, the amounts are detected by sensing the level of fluid in each reservoir during (i.e., in a real-time manner) or after filtration.

Filtration may be performed in several cycles in which the admixture is only partially depleted of buffer to maintain the viability of the biological component. Several cycles of buffer exchange may be performed until a target exchange is achieved (e.g., at least about 95%, at least about 99% or even at least about 99.9% of the first buffer has been exchanged by the second buffer).

After filtration, the chamber 19 is depressurized and the chamber door 11 (FIG. 1) is opened. An X-Y stage 70 (FIG. 9) moves to the chamber opening, secures the filtration wells and removes them from the chamber and carries the reservoirs to a sensing station. At the sensing station, a sensor 72 such as a non-contact height sensor detects the amount of first buffer solution removed from each reservoir. Alternatively, the sensor may be present in the pressure chamber 19 to measure, in situ, the amount of first buffer removed from the reservoirs.

The sensor 72 may generate a signal relating to the detected amount of first buffer that was removed from the individual reservoirs to a control system (not shown) operable to control a dispensing system for dispensing the second buffer solution into the reservoirs. The amount of second buffer added to each reservoir may be based on the detected amount of first buffer that was removed from the reservoir (e.g., based on the sensed level of the buffer-depleted residue in the reservoir). The dispensing system may include an X-Y stage 70 and dispenser 82 (i.e., dispense tip). In some embodiments, the reservoirs are transferred from the pressure chamber 19 to another work station in the system for adding second buffer to each reservoir. In other embodiments, the second buffer is added with the filtration reservoirs in situ.

After the desired degree of exchange of the second buffer is achieved, the biological component may be further processed (e.g., surfactant added) and/or analyzed. In some embodiments, the biological components of the reservoirs are pooled for further processing or analysis.

The buffer exchange system (FIG. 9) may include additional stations and vessels for buffer exchange including a plurality of buffer source containers 94, a dispenser waste vessel 84, protein supply 98, surfactant supply 86, dispense tips 88, a final formulation station 96, an admixture temperature control device (not shown) and/or a priming and calibration station 90.

Figure 10:
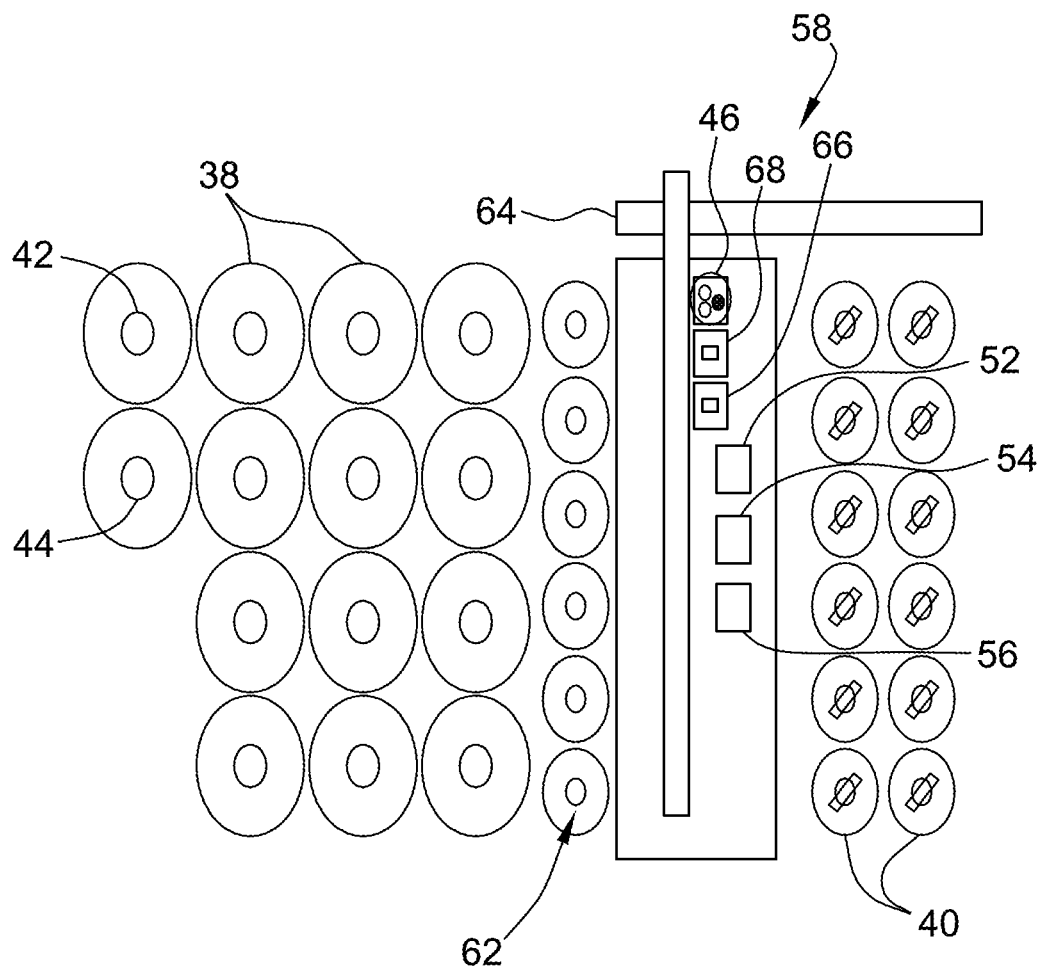
FIG. 10 is a schematic view of an API formulation system.

A system 58 suitable for formulation preparation and exchange of active pharmaceutical ingredient (API) into the formulation of interest using the buffer exchange processes described above is shown in FIG. 10. The system 58 includes an x-y stage 64, dispense tips (e.g., X6, X12) 66, 68, pH wash station 52, priming station 54 and calibration station 56. The system 58 also includes various excipients 62, formulation receptacles 38, stock buffers 40, titration and buffer storage 46 and acid (e.g., HCL) storage 42 and base (e.g., NaOH) storage 44.

Figure 11:
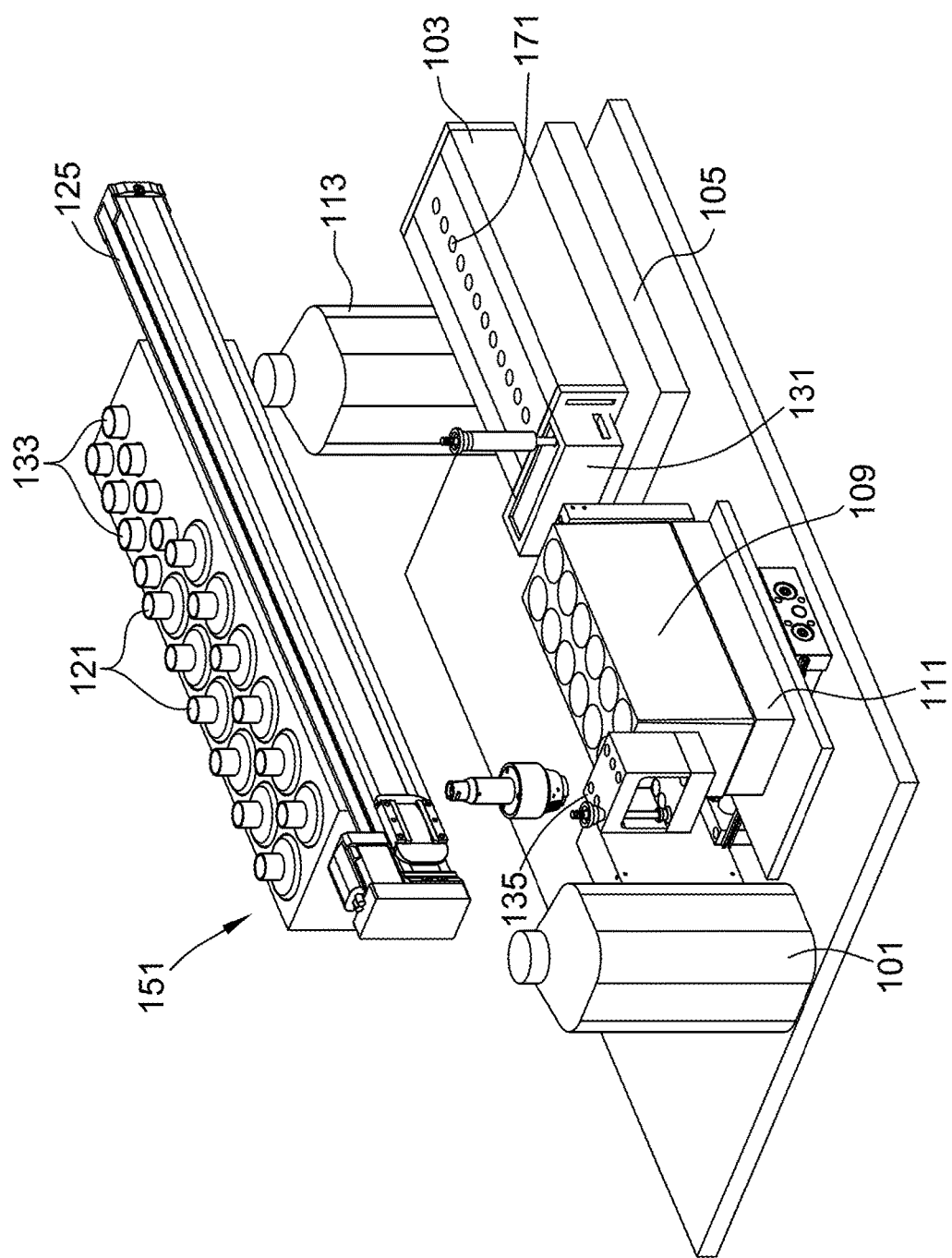
FIG. 11 is a schematic view of another embodiment of a buffer exchange system.

Another embodiment of a system 151 for formulation preparation and exchange of buffers is shown in FIG. 11. The system 151 is used to prepare working formulation (e.g., formulation with specific pH) and concentrations from stock buffers and excipients and exchanges the biological component (e.g., protein) of interest into these working formulations.

The system 151 includes a filtration unit or "buffer exchange module" 103. In the illustrated embodiment, the filtration unit 103 includes openings 119 (FIG. 13) to receive and form an air-tight seal with six formulation reservoirs (not shown) having a semi-permeable membrane. The filtration unit 151 may include more or less openings 119 (e.g., at least 2, at least 3, at least 5, at least 10, at least 12, at least 16, at least 48 or at least 96 reservoirs). A working formulation having a biological component and a first buffer solution is prepared in or transferred to each reservoir (not shown). Components may be added through the reservoirs through access openings 171 (FIG. 12) formed in a cover 175 for sealing the reservoirs.

The buffer exchange module 151 is pressurized to force the first buffer through the semi-permeable membrane and out of the reservoirs. Pressurization may be achieved by injecting an inert gas such as $N_2$ into the reservoirs to enable a higher rate of filtration. A second buffer solution is introduced into the reservoirs during or after removal of the first buffer solution.

The liquid level in each reservoir may be measured and monitored real-time using the pressurized inert gas. The time needed to pressurize an individual reservoir at a given pressure with a given inert gas flow is measured and used to calculate the total void volume in the reservoir. The real-time monitoring of volume in the reservoir may then be further used to calculate the real-time flow rate through the semi-permeable membrane.

Refill of the second buffer solution may be done programmatically given the real-time volume feedback. For example, the system 151 may include a controller programmed to refill a reservoir (1) once a specified volume is reached, (2) once a predetermined time is reached, or (3) after a combination of volume and time as algorithmically calculated to minimize the buffer exchange process time. The second buffer solution may be added to (1) maintain a constant concentration of biological component in solution while performing a buffer exchange, (2) maintain a maximum concentration of biological component in solution while performing a buffer exchange, or (3) concentrating the biological component to a programmable value.

Similarly, vortexing can be activated programmatically given the real-time volume feedback (i.e., dynamic vortexing may be used). The system 151 may include a controller programmed to control vortexing (1) to begin once a specified minimum flow rate is reached, (2) to maintain a constant flow rate, (3) to begin at a set time/schedule, or (4) as a function of flow rate and time as algorithmically calculated to achieve a desired buffer exchange process time with minimum vortexing.

The exchange process is continued until the target percent exchanged is achieved. Typically exchange cycles are repeated until at least about 95%, at least about 99% or even at least about 99.9% of buffer has been exchanged. Once an exchange is complete, the system may add a target amount of surfactant to each formulation. The reservoirs (not shown) containing the fully exchanged formulations may be removed from the filtration unit 103 for further processing.

Mixing of the reservoir contents during filtration may be done by vortexing. The filtration unit 103 includes a vortexing unit 105 that rapidly oscillates in a circular or orbital motion to create a vortex within the admixture. The vortexing unit 105 may operate in a manner similar to the unit 99 (FIG. 4) described above. The vortexing unit 105 may also be used for temperature control of the admixtures by, for example, circulation of heating or cooling fluids.

The system 151 may include an x-y stage 125 and may include additional stations and vessels for buffer exchange. Additional stations and vessels include protein stock vessel 131, paired buffer source vessels 121, dispenser waste vessel 101, wash vessel 113, excipient vessels 133, working buffer station 109 with stirring unit 111 and surfactant supply 135.

EXAMPLES

The processes of the present disclosure are further illustrated by the following Examples. These Examples should not be viewed in a limiting sense.

Figure 12:
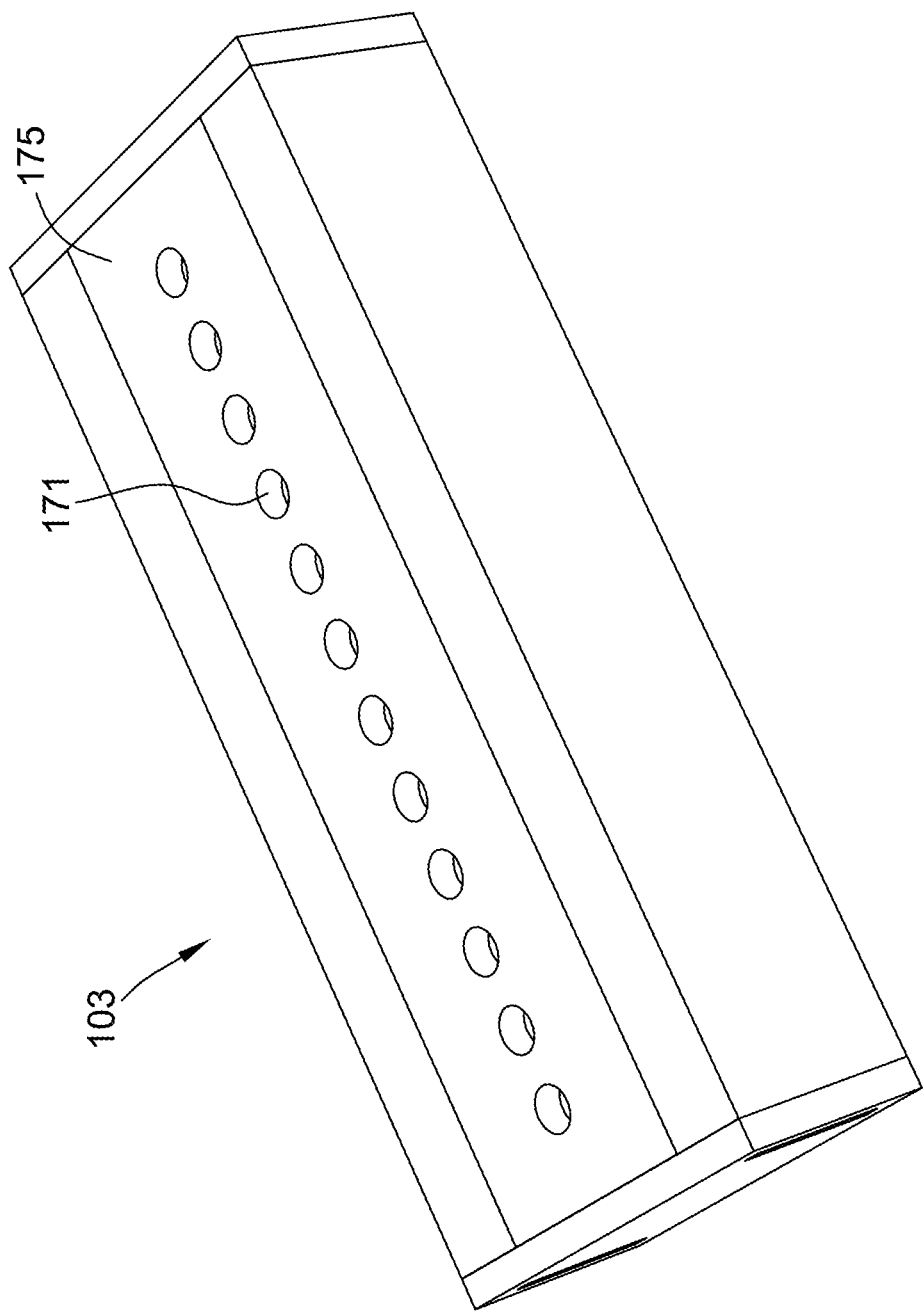
FIG. 12 is a perspective view of the filtration unit of FIG. 11.
Figure 13:
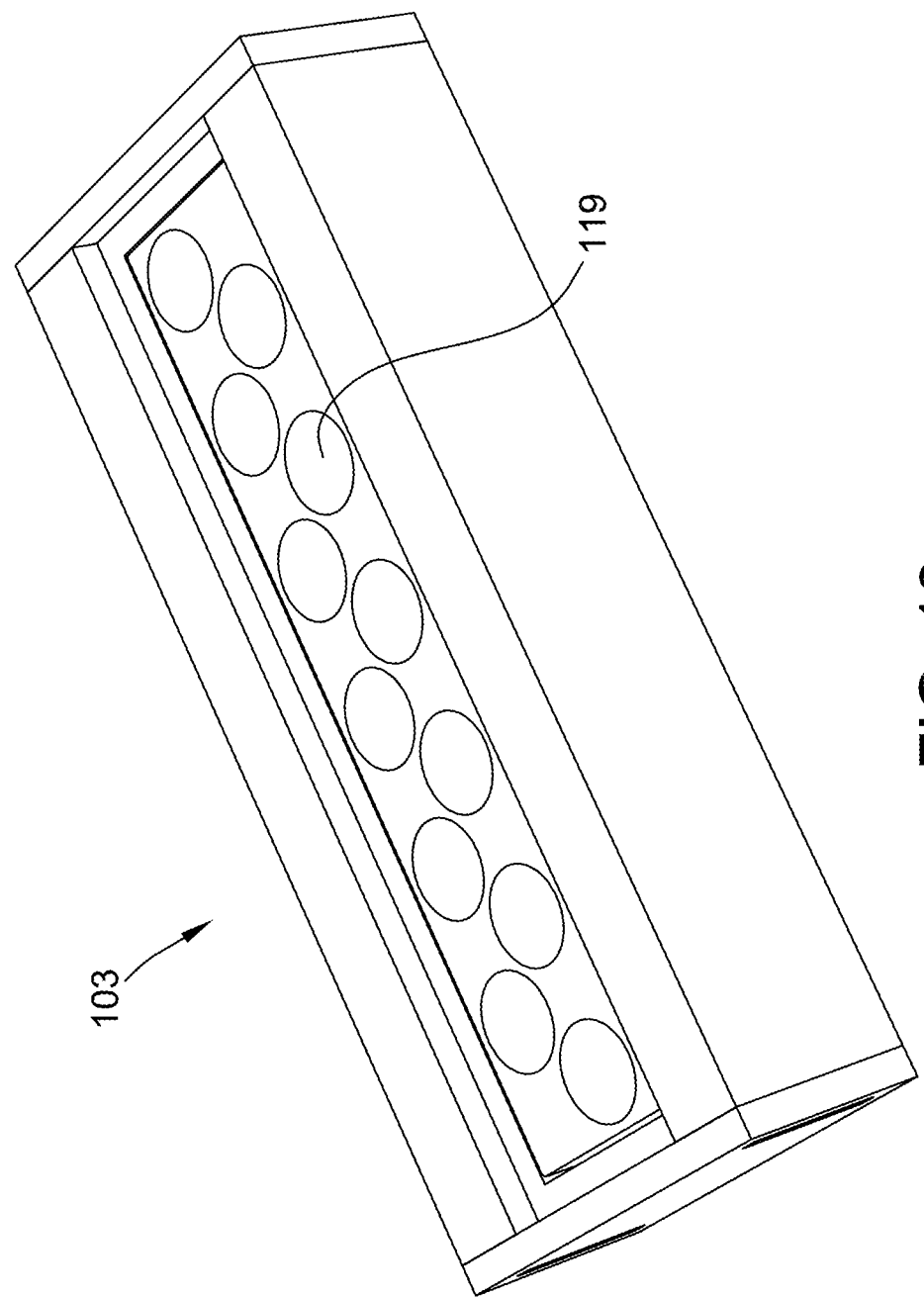
FIG. 13 is a cross-sectional perspective view of the Filtration unit of FIG. 11.
Figure 14:
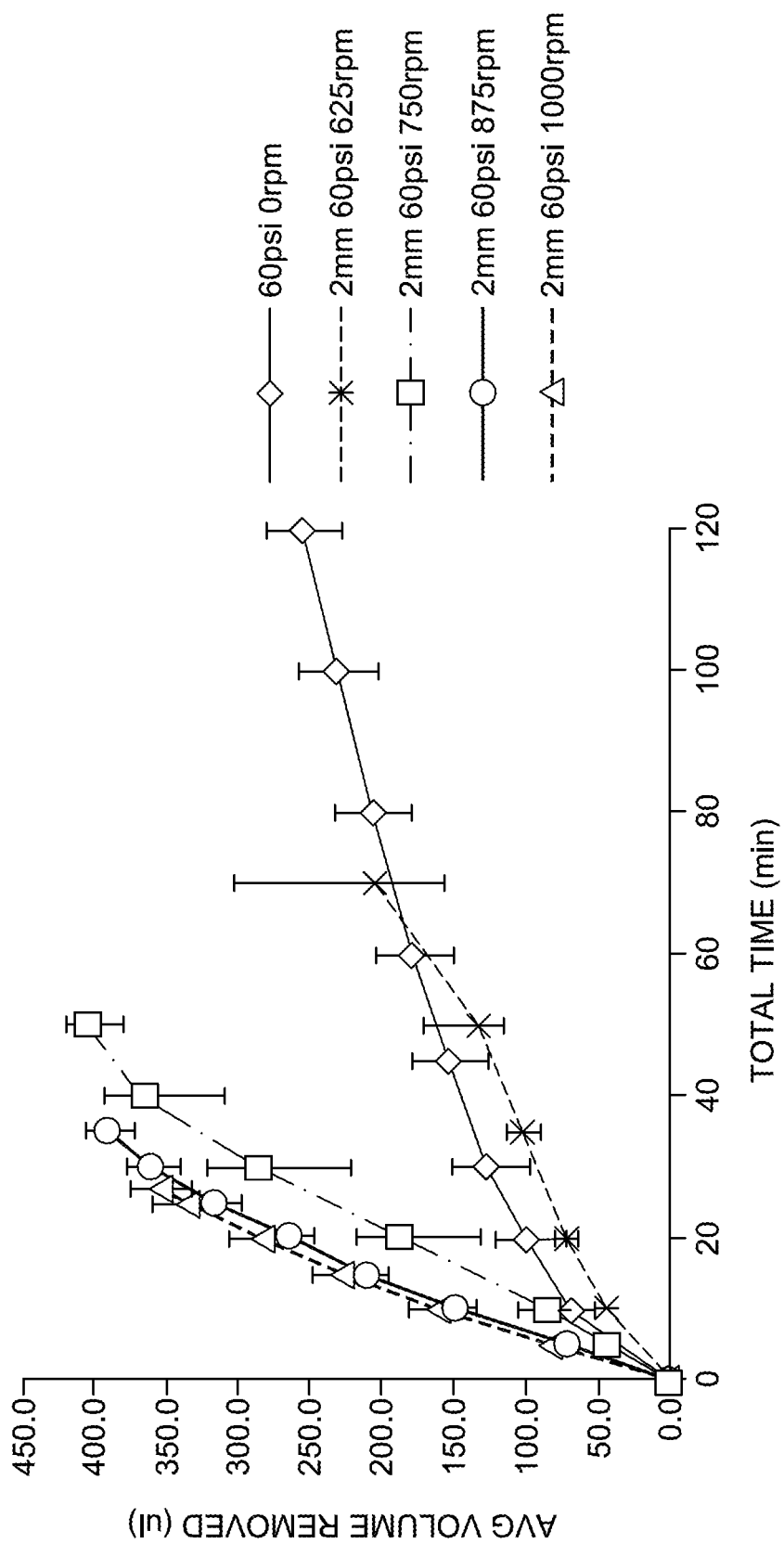
FIG. 14 is a graph of the filtration volume over time at different vortexing RPM.

Example 1: Comparison of Oscillation Rate on the Filtration of IgG Antibody in PBS The graph of FIG. 12 shows filtration rates of 10 mg/mL IgG antibody in 1X Phosphate Buffered Saline (PBS) using 60 psi pressure and a 2 mm orbital for vortexing with variable RPM.

Example 2: Filtration of IgG Concentration Polyclonal IgG Antibody

High concentration polyclonal IgG was recovered under the following conditions:
Polyclonal IgG concentration: 72 mg/mL (approximate extinction coefficient: 1.4 AU per 1 mg/mL)
Buffer: PBS pH 6.98
Exchange buffer: PBS pH 5.98
Buffer-exchange module prototype and CM3 were used to perform six pressure-mixing and refilling cycles on the above sample in a 96 well microtiter plate
Each cycle was about 90 minutes (77 min pressure cycle to filter 50% volume, 3 min level check, and 10 min for liquid addition)
Post filtration, material from wells of a 96 well microtiter plate were pooled manually, but this step can be performed with an automated system as well
UV and pH were measured on a 15 mL aliquot from the ~38 mL of exchanged material

TABLE 1

| UV Data Pre- and Post-Buffer Exchange | | | |
|---|---|---|---|
| UV Data Pre-Buffer Exchange A280 with pathlength correction | | | |
| Prep 1 | Prep 2 | Prep 3 | Average |
| 0.822 | 0.835 | 0.849 | 0.835 |
| Pre-buffer ExchangeConcentration (mg/mL) 72 | | | |
| UV Data Post-Buffer Exchange A280 with pathlength correction | | | |
| Prep 1 | Prep 2 | Prep 3 | Average |
| 0.841 | 0.862 | 0.820 | 0.841 |
| Pre-buffer ExchangeConcentration (mg/mL) 72 | | | |

Substantially no protein loss was observed after the buffer exchange.

As used herein, the terms "about," "substantially," "essentially" and "approximately" when used in conjunction with ranges of dimensions, concentrations, temperatures or other physical or chemical properties or characteristics is meant to cover variations that may exist in the upper and/or lower limits of the ranges of the properties or characteristics, including, for example, variations resulting from rounding, measurement methodology or other statistical variation.

When introducing elements of the present disclosure or the embodiment(s) thereof, the articles "a", "an", "the" and "said" are intended to mean that there are one or more of the elements. The terms "comprising," "including," "containing" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above constructions and methods without departing from the scope of the disclosure, it is intended that all matter contained in the above description and shown in the accompanying drawing [s] shall be interpreted as illustrative and not in a limiting sense.

What is claimed is:
1. A system for automated exchange of buffer solutions from admixtures comprising a first buffer solution and a biological component, the system comprising:
   a pressure chamber containing a receiver plate, the plate comprising a plurality of reservoirs, wherein each reservoir of the plurality of reservoirs contains a semipermeable membrane;
   a pressure regulator configured to create a pressure difference across the semi-permeable membranes that forces the first buffer solution through the semi-permeable membranes to produce a filtrate and a first buffer-depleted residue in the reservoirs;
   a sensing station comprising a sensor for detecting a volume of the filtrate in each reservoir; and
   a dispensing system for adding a volume of a second buffer solution to each reservoir;
   wherein, for each reservoir, the volume of the second buffer solution matches the sensed volume of the filtrate.

2. The system of claim 1, further comprising a mixer.

3. The system of claim 2, wherein the mixer is a vortex mixer.

4. The system of claim 1, further comprising a waste container for collecting the filtrate from the plurality of reservoirs.

5. The system of claim 1, further comprising a temperature control device for controlling the temperatures of the admixtures.

6. The system of claim 1, further comprising a plurality of buffer source containers.

7. The system of claim 1, further comprising a control system operable to control the dispensing system for dispensing the second buffer solution into each reservoir based on a signal from the sensor.

8. The system of claim 1, wherein the sensor is operable for acoustic sensing, capacitance sensing, light reflectance sensing, displaced air volume sensing or weight measurement of the produced volumes of filtrate.

9. The system of claim 1, wherein the semi-permeable membranes are characterized by a molecular weight cut off of about 100 kDa or less.

10. The system of claim 1, wherein the semi-permeable membranes are characterized by a molecular weight cut off of about 10 kDa or less.

11. The system of claim 1, wherein each reservoir has a volume ranging from about 250 ul to about 75 ml.

* * * * *